United States Patent [19]

Mirelman et al.

[11] Patent Number: 5,071,742

[45] Date of Patent: Dec. 10, 1991

[54] ASSAY FOR AMOEBAE AND PROBES FOR USE THEREIN

[75] Inventors: David Mirelman, Ramat Efal; Leonard I. Garfinkel, Rehovot; Michael Giladi, Tel-Aviv, all of Israel; Marion Huber, Stuttgart, Fed. Rep. of Germany; Carlos Gitler; Michel Renel; Shmuel Rozenblatt all of Rehovot, Israel

[73] Assignee: Yeda Research and Development Co., Ltd., Rehovot, Israel

[21] Appl. No.: 402,700

[22] Filed: Sep. 5, 1989

[30] Foreign Application Priority Data

Sep. 4, 1988 [IL] Israel ..................................... 087668

[51] Int. Cl.$^5$ ..................... C12Q 1/68; G01N 33/566; G01N 33/00
[52] U.S. Cl. .......................................... 435/6; 536/27; 436/501; 436/94
[58] Field of Search .............. 435/6; 536/27; 136/501; 436/94

[56] References Cited

FOREIGN PATENT DOCUMENTS

| 135108 | 3/1985 | European Pat. Off. | ................ 435/6 |
| 0135108 | 3/1985 | European Pat. Off. | ................ 435/6 |
| 235727 | 9/1987 | European Pat. Off. | ................ 435/6 |
| 0235727 | 9/1987 | European Pat. Off. | ................ 435/6 |

OTHER PUBLICATIONS

Bhattacharya et al., Molecular and Biochemical Panasitology, vol. 27 (1988) 257–262 published Jan. 15, 1988.
"Abstracts of Papers", Gastroenterology, vol. 92, No. 5, Part 2, p. 1612; Samuelson et al.
"Proc. Natl. Acad. Sci. U.S.A.", (1989), vol. 86, pp. 5118–5122, (7/1989), *Geomic DNA Differneces between Pathogenic an Nonpathogenic Entamoeba Histoyltica;* Tannich et al.
"Journal of Clinical Microbiology", vol. 27, No. 4, (1989), pp. 671–676, *DNA Hybridization Probe for Clinical Diagnosis of Entameoba Histolytica;* Samuelson et al.
"Infect. Immun.", vol. 57, No. 3, (1989), pp. 926–931, *DNA Probes Specific for Entamoeba Histolytica Possessing Pathogenic and Nonpathogenic Zymoclemes;* Garfinkel et al.
Abstract in Gastroenterology Samuelson et al. (copy not attached).

*Primary Examiner*—Robert A. Wax
*Assistant Examiner*—Eric Steffe
*Attorney, Agent, or Firm*—Browdy and Neimark

[57] ABSTRACT

An assay for the determination of the presence or absence of *E. histolytica* and for differentiation of these from other types of amoebae, as well as for the determination of whether the *E. histolytica* belongs to a symptomatic or asymptomatic strain, is carried out by means of a DNA-probe adapted to selectively hybridize only to the DNA of the amoeba tested. The probes being used selectively hybridize with, and thus diagnose the presence of, symptomatic (pathogenic) and asymptomatic (non-pathogenic) strains, respectively.

18 Claims, 8 Drawing Sheets

DNA DOT BLOT HYBRIDIZATION

| E.histolytica strain | 1μl | 2μl | cpm | cpm |
|---|---|---|---|---|
| CDC:0784:4 | ● | ● H6.6 | 2808 | 4406 |
| SAW 1734R | ● | ● | 7113 | 11428 |
| HM-1 | ● | ● | 15449 | 28172 |
| CDC:0784:4 | | P 145 | 36 | 73 |
| SAW 1734R | | | 19 | 44 |
| HM-1 | ● | ● | 7213 | 11444 |
| SAW 755 | ● | ● | 402 | 657 |
| HM-1 | | B 133 | 9 | 38 |
| SAW 1734R | ● | ● | 1056 | 2001 |
| CDC:0784:4 | ● | ● | 881 | 1005 |
| SAW 755 | | | 32 | 75 |

FIG. 6

| E. HISTOLYTICA STRAIN | PROBE P145 | PROBE B133 |
|---|---|---|
| SAW 408 | | |
| HM-1:IMSS | | |
| SAW 760 | | |
| SAW 1734 R | | |

```
         10         20         30         40         50         60
GATCGATTTT CCCAGTTAGA AATTATTGTA CTTTGTATTT AGTACTTTTC ATTAAAAATG
         70         80         90        100        110        120
GTGAGGTTCT TAGGAAATCC GAAAATCAAC GGTGTAAATT GGTCAAAAAA TATTTTGCCT
        130        140
AGACGACGAC CATTTTGAAT AATTCGATC
```

FIG. 8b

```
         10         20         30         40         50         60
GGATCCTCCA AAAAATAAAG TTTTATCAGA AATGGTGAGG TTGTAGCAGA GATATTAATT
         70         80         90        100        110        120
CAACAATTTT ATTGAAAAAA GGTGCACTTT TTTGATTTTA ATATAAAGTA CTAGTATCC
        130
AATATCGTTC TGTGGATCC
``` a -- 5' -- TGA ATT AAT ATC TCT GCT AC -- 3' b -- 5' -- CGA TAT TGG ATA CCT AGT AC -- 3' c -- 5' -- TCT AAC TGG GAA AAT CGA TC -- 3' d -- 5' -- CAA AAT GGT CGT CGT CTA GGC -- 3'

FIG. 9

ASSAY FOR AMOEBAE AND PROBES FOR USE THEREIN

FIELD OF THE INVENTION

The present invention relates to an assay for determining the presence or absence of pathogenic and non-pathogenic isolates of *Entamoeba histolytica*, and for the differentiation between these. The invention further relates to specific DNA-probes which selectively hybridize to the DNA of *E. histolytica* isolates that have zymodemes that are either pathogenic or nonpathogenic. The probes of the invention are based on tandemly repeated complementary DNA sequences which are specific to each type of the isolates. Such probes, adequate for hybridization, preferably have a length of approximately 20 base pairs, and make possible rapid and direct diagnosis of such amoeba species.

BACKGROUND OF THE INVENTION

*E. histolytica*, which is the causative agent of amoebiasis, inhabits the intestinal tract of nearly one-half billion people worldwide and leads to about 75,000 deaths per year (1). The majority of infected persons are asymptomatic carriers. Histolytica isolates from symptomatic individuals have been shown to differ in the electromobility of certain isoenzymes (zymodemes) from those of amoebae obtained from most asymptomatic carriers. This has been the basis for the designation of "pathogenic" and "non-pathogenic" strains (2). Clinical diagnosis of *E. histolytica* by zymodeme typing is slow, the process usually requiring several days to complete.

The connection between zymodemes and pathogenicity as well as its molecular basis is still unknown (3,4).

SUMMARY OF THE INVENTION

The present invention relates to an assay for determining the presence or absence of pathogenic and non-pathogenic isolates of *Entamoeba histolytica*. More particularly, the present invention relates to a DNA sequence which is complementary or identical to a part of a strand of the DNA of *Entamoeba histolytica*, and which probe is of adequate length for hybridizing to the DNA of the amoeba under high stringency conditions, and thus to serve as a probe for establishing the absence or presence of the specific type of amoeba. Preferably, the DNA sequence has a length of about 20 base pairs. The DNA probe chosen for carrying out the assay of the present invention is a direct or complementary sequence of all or part of one of the repetitive sequences of an extrachromosomal element containing ribosomal DNA; preferred chosen sequences have a high content of guanosine and cytosine residues. It has been found that non-pathogenic amoeba have a repetitive region in an analogous extrachromosomal molecule consisting of 133 base pairs, whereas pathogenic *Entamoeba histolytica* have a repetitive sequence of 145 base pairs. The sequence homology between the two elements is less than 40%.

Thus, there is provided an assay for pathogenic amoeba histolytica which comprises reacting the amoeba to be tested with a DNA probe with a sequence as defined above, specific for pathogenic or for non-pathogenic amoeba, and establishing whether or not such probe hybridizes to the amoeba. The material required for the assay of the invention can be supplied in kit form, adapted for single as well as for multiple tests at a time. In such a kit there are provided support means for the samples, a supply of DNA in suitable form in unit dosage or multiple dosage form, buffers, solvents and other reactants, and detection means for the labelled probe.

Advantageous results were obtained in detection assays for amoeba with non-pathogenic zymodemes when the complementary sequence of base pairs 44 to 63 or 110 to 129 of the 133 base pair units; and for *E. histolytica* bearing pathogenic zymodemes when the complementary sequence to base pairs 1 to 20 or 119 to 138 of the 145 base pair repetitive sequences were used. The nucleic material of the amoeba to be tested is advantageously supported by a suitable support, such as nitrocellulose or nylon-based membrane filters, agarose gels, or the like. It is possible to provide the DNA probes with suitable radioactive tags, with enzymes or ligands bound to them, etc. The amoeba is treated so as to expose the DNA of same, such treatment being possible with a suitable alkali, detergent, or the like. The DNA is immobilized on a small area of the support membrane or the like, and subjected to hybridization with the DNA probe under high stringency conditions. After removal of excess of the non-hybridized probe material, one can determine whether any labelled DNA remains attached to the sample.

DETAILED DESCRIPTION OF PREFERRED EMBODIMENTS

Materials and Methods:
Entamoeba isolates and culture conditions.
a) *E. histolytica* strains with pathogenic zymodemes used in this study were the following: The axenic strains HM-1:IMSS c16, 200:NIH, and Rahman were obtained from Dr. L. S. Diamond (NIH, MD). Another axenic culture of HM-1:IMSS was provided by Dr. J. I. Ravdin (Charlottesville, Va). Strains SAW 1734 clAR and CDC:0784:4 were axenized by L. S. Diamond from xenic cultures which originally possessed non-pathogenic zymodemes and had converted to pathogenic ones during the process of axenization (3,4). All these above mentioned strains were grown in axenic medium TYI-S-33 (5) in plastic flasks (40 ml). Two additional strains with pathogenic zymodemes SAW 408 (zymodeme group II) and SAW 755 group XIV, originating from P. G. Sargeaunt, London School Hygiene and Tropical Medicine) were grown together with their original bacterial associates in TYSGM-9 medium (6).

b) Xenic strains of *E. histolytica* with non-pathogenic zymodemes used in this study were the following: SAW 1734R clAR (group III), SAW 760 (group IX), CDC:0784:4 (group I) and WI:1285:1 (group I). The first two strains were originally isolated by and obtained from P. G. Sargeaunt. These strains were cultured both in TYSGM-9 medium (6) as well as in TYI-S-33 medium (5), together with a reduced bacterial flora in the presence of an antibiotics mixture (Cefotaxime, Erythromycin and Amikacin at final concentrations of 50 μg/ml each) (3). The last two strains were grown together with their bacterial associates only in TYSGM-9 medium (4).

c) *E. histolytica. var Laredo, E. Moshkovsky* and *E. invadens* strain IP-1 were also obtained from L. S. Diamond and grown axenically in TYI-S-33 medium at 27° C.

The "pathogenic" or "non-pathogenic" isoenzyme pattern of each of the cultures was confirmed by the electrophoretic migration of the hexokinase and phosphoglucomutase isoenzymes as described (3,4).

Construction of genomic libraries.
a) DNA from *E. histolytica* HM1:IMSS c16 was prepared as described (7), digested with EcoRI or HindIII, and inserted into EcoRI or HindIII digested pUC-18 DNA, and transformed into *Escherichia coli* strain DH1 (8). Clones containing highly abundant genomic DNA sequences were identified by colony filter hybridizations with nick-translated total genomic DNA as probe. Hybridizations were carried out as described (7). This screening yielded probes H6.6, R2.3, R715 and H4.4 with insert sizes of 6.6 kb, 2.3 kb, 0.9 kb and 4.4 kb, respectively. An additional clone, H16, with a 14.3 kb insert contained a repetitive fragment of 145 b.p. which was released by digestion with Sau3AI and subcloned in the BamHI site of pUC-18. This subclone was designated P145.

b) DNA from the non-pathogenic strain *E. histolytica* SAW 1734R clAR was prepared as described (7) from trophozoites grown in the presence of reduced amounts of associated bacterial cells and starch particles. Xenic cultures of this organism were grown in TYI-S-33 medium (5) in 40 ml plastic flasks containing a mixture of antibiotics consisting of Cefotaxime, Erythromycin and Amikacin, at a final concentration of 50 μg/ml. BglII digested DNA was cloned in the BamHI site of pUC-8 and screened by hybridization with clone R715 (see Results) giving clone B2342. This clone had a 11.5 kb insert which contained a tandemly repeated BamHI fragment of 133 b.p. A 3.0 kb EcoRI fragment containing these reiterated units was subcloned in EcoRI-digested pUC-8 as clone B 3.0 and the 133 b.p. BamHI repeat element was also subcloned in pUC-8 and designated B133.

DNA sequence analysis.
DNA sequencing was performed according to the method of Sanger et al. (9) after subcloning of restriction fragments into the phage vectors M13 mp18 (10). Sequence data were analyzed using the MicroGenie program (Beckman) and the Fast P program of David J. Lipman and William R. Pearson (11).

Southern blot hybridizations.
Genomic DNA (approximately 0.5 μg) isolated from the various Entamoeba strains was digested with EcoRI, size fractionated on 0.8% agarose gels in TAE buffer, pH 7.8 (Tris HCl, 100 mM, sodium acetate, 50 mM, EDTA, 5 mM) transferred to nitrocellulose or nylon membranes and hybridized as described (7). DNA probes were labelled by nick-translation or by random priming. Exposures for 2 hours using two intensifying screens at −70° C. were generally sufficient to give strong signals. For re-use, blots were treated three times with buffer containing 0.01X SSC, 0.01% sodium dodecyl sulfate (SDS) for 5 minutes at 100° C. in order to remove previously hybridized probe. Removal of probe was verified by autoradiography. DNA dot blot hybridizations were done under high stringency as described (7). In brief, hybridization was carried out in formamide (50%) at 42° C. over night. First, three washings were done with 2×SSC and 0.1% SDS at 65° C. for 20 minutes. Then, two more rapid washings at room temperature with 0.1×SSC and 0.1% SDS were done.

Hybridizations intact trophozoites on Zetapore filters.

Trophozoites ($2 \times 10^5$ cells) grown in either of the culture media used were harvested after chilling (5 min) and resuspended in TYI-S-33 medium (5 ml without serum). The suspension containing the trophozoites was passed through a Zetapore membrane filter on a Buchner funnel using a weak suction. The cells were washed with phosphate buffered saline and the Zetapore filter was placed for 15 min on a Whatman 3 MM filter saturated with a solution of detergent NP-40 (1%) in TAE buffer containing 25 μg/ml protease K. The Zetapore filter was blotted several times over a dry Whatman 3 MM filter and then placed on another Whatman 3 MM filter saturated with a DNA denaturing solution consisting of NaOH 0.5M and NaCl 1.5M. Intermittent blotting was performed for 15 min, after which the Zetapore filters were neutralized by placing them on an additional Whatman 3 MM filter saturated with Tris buffer pH 7.4 and NaCl 1.5 M. After this step the filters were washed, cut into halves and hybridized with probes P145 or B133, as described above for Southern blots.

Results

Upon digestion of HM1:IMSS DNA with EcoRI and size fractionation on agarose gels, a distinct series of bands was visible after staining with ethidium bromide. HindIII digestion similarly resulted in a number of distinct bands. These bands indicate the presence of highly abundant DNA sequences. A number of these elements were cloned as a first step toward understanding the DNA sequence organization of E. histolytica. Using the procedures detailed in Materials and Methods, several subclones were obtained, of which H16, H6.6, R2.3, R715 and H4.4 are described in this paper. Clone B3.0 was subcloned from a highly abundant BglII fragment from the DNA of the non-pathogenic E. histolytica isolate SAW 1734R clAR.

Figure 1:
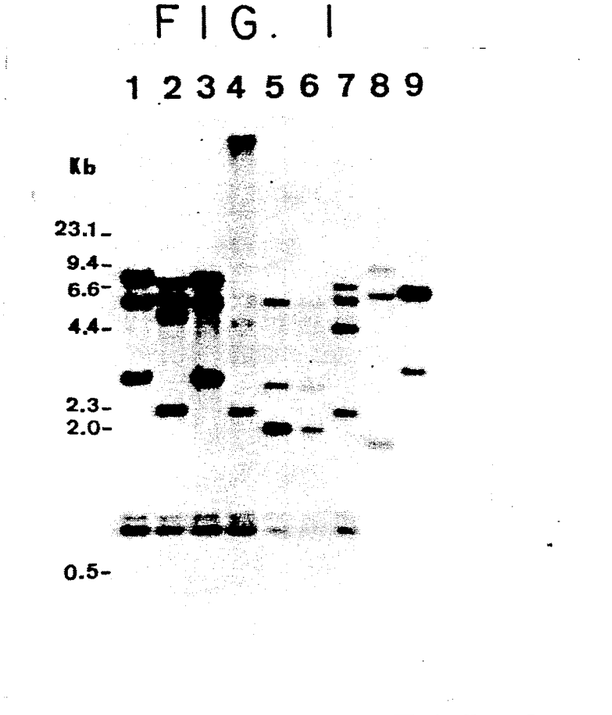
FIG. 1 is a Southern blot showing the classification of *E. histolytica* isolates based on hybridization patterns using probe H6.6. The Southern blot shown contains EcoRI digested DNAs from the following sources: Lanes 1-7, *E. histolytica* isolates. Lane 1, Rahman; lane 2, HM1:IMSS (from J. I. Ravdin); lane 3, 200:NIH; lane 4, HM1:IMSS c16 (from L. S. Diamond); lane 5, SAW 1734R clAR (from P. G. Sargeaunt); lane 6, WI:1285:1; lane 7, CDC:0784:4 (axenic culture from L. S. Diamond). Lane 8, *E. histolytica* var *Laredo* lane 9, *Entamoeba invadens*.

DNA of several strains of E. histolytica with pathogenic and non-pathogenic zymodemes was digested with EcoRI, size fractionated on agarose gels and transferred to nitrocellulose filters. FIG. 1 shows the hybridization pattern obtained after probing one such filter with H6.6, a probe derived from a genomic library of HindIII-digested E. histolytica HM1:IMSS c16 DNA in plasmid pUC-18. The autoradiogram shown in FIG. 1 contains DNA from several isolates of E. histolytica as well as DNA from E. histolytica var Laredo, a variant of E. histolytica with altered growth characteristics and generally regarded as a different species from E. histolytica (12, 13) and Entamoeba invadens, a low temperature growing species which infects reptiles. Two main trends are immediately apparent in FIG. 1. First, all of the E. histolytica isolates have two bands (0.8 kb and 0.9 kb) in common. These bands are absent in the non-histolytica strains Entamoeba invadens and E. histolytica var Laredo. Second, there is variability in the hybridization patterns obtained from the various E. histolytica strains. One class of isolates consisted of the axenically grown strains HM1:IMSS, HM1:IMSS c16 and CDC:0784:4 (lanes 2,4,7), all of which possessed pathogenic zymodeme group II. Strains Rahman and NIH:200 (lanes 1 and 3). which also have pathogenic zymodeme group II comprise a second class. Strains SAW 1734R clAR and WI:1285:1 which possess non-pathogenic zymodeme (groups III and I, respectively) (lanes 5 and 6) comprised a third class.

Figure 2A:
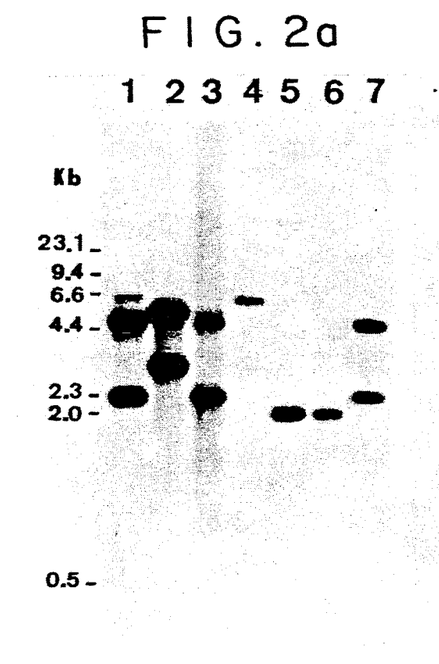
FIG. 2 is a Southern blot hybridization using probes which demonstrate differences (A) and similarities (B) between isolates. Southern blot hybridizations shown in (A) and (B) were both prepared from the same blot after removing probes as described in Materials and Methods. (A), probe R2.3; (B), probe R715. Isolates used were: lane 1, HM1:IMSS; lane 2, NIH:200; lane 3, HM1:IMSS c16; lane 4, *E. histolytica* var *Laredo*; lane 5, SAW 1734R clAR; lane 6 WI:1285:1; lane 7, CDC:0784:4.
Figure 2B:
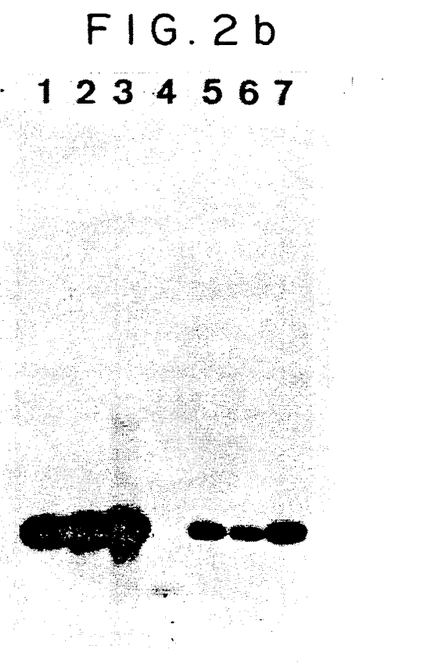

Some of our probes highlight specific subsets of the bands visible in FIG. 1. Thus, probe R2.3, also derived from HM1:IMSS c16, gives the pattern seen in FIG. 2a. This pattern, although simpler than that of FIG. 1, still allows the classification of the strains into the same three groups. Another probe derived from HM1:IMSS c16, R715, hybridized to only one band common to all of the E. histolytica strains, as shown in FIG. 2b. This probe did not hybridize to E. histolytica var Laredo or E. invadens (latter not shown).

Figure 3A:
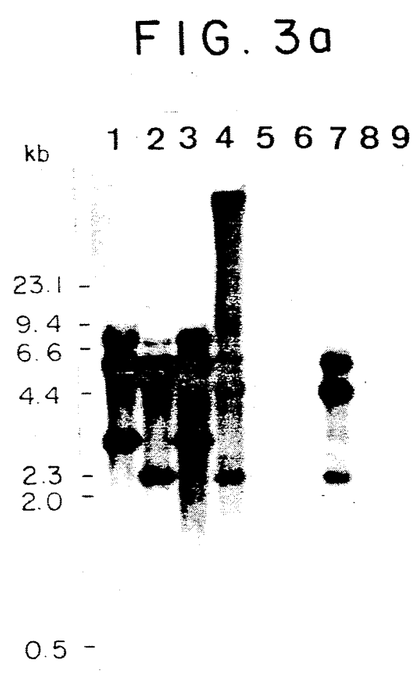
FIG. 3 is a Southern blot hybridization using probe H4.4 in A and probe P145 in B. A shows that probe H4.4 hybridizes exclusively to DNA from pathogenic isolates of *E. histolytica*. Samples are the same as in FIG. 1. B shows that probe P145 hybridizes exclusively to DNA from pathogenic isolates of *E. histolytica*. Samples are the same as in FIG. 1.

As shown in FIG. 3a, probe H4.4 which was also derived from strain HM-1:IMSS c16, does not hybridize to DNA from E. histolytica strains SAW 1734R clAR and WI:1285:1 which have nonpathogenic zymodemes. The striking absence of hybridization by H4.4 to DNA of SAW 1734R clAR and WI:1285:1 indicates that these isolates lack some of the DNA sequences common to all the other pathogenic E. histolytica strains tested. Moreover, the probe does not hybridize to DNA of E. histolytica var Laredo (lane 8). Entamoeba invadens (lane 9) or to rat DNA (not shown). The fact that this probe did not hybridize to certain E. histolytica strains was not due to lack of amebic DNA on the blots or to dilution by bacterial DNA originating from the xenic cultures. Sufficient amebic DNA was present as seen by reprobing the same blots with probe R715, which hybridized to the common bands (0.8 and 0.9 kb, FIG. 2B) or with probe B3.0 (FIG. 4).

Figure 3B:
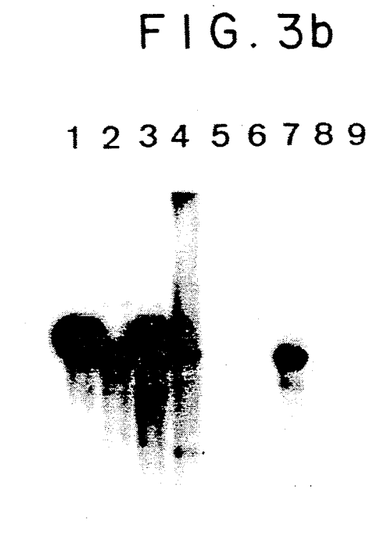
Figure 5:
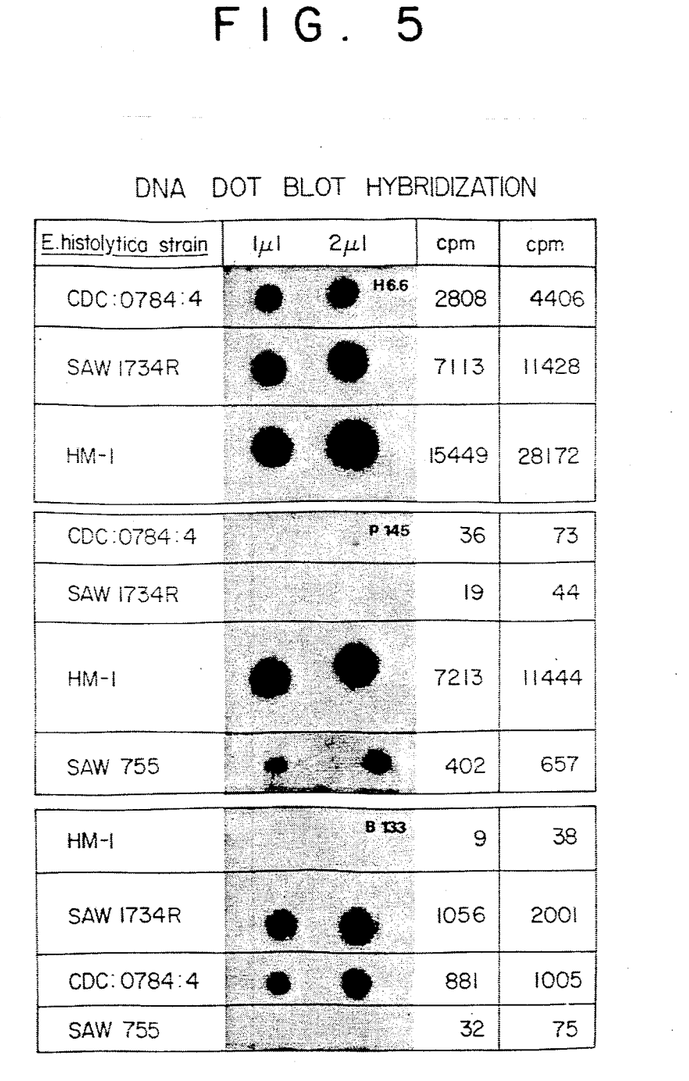
FIG. 5 shows the results of DNA dot blot hybridization using DNA from various strains of *E. histolytica*. The DNA were hybridized on Zetapore membranes with probes H6.6, P145 and B133. Strains CDC:0784:4 and SAW 1734R clAR had non-pathogenic zymodemes, whereas strains HM-1:IMSS and SAW 755 had pathogenic ones. Strains CDC:0784:4 and SAW 755 were grown with their bacterial flora in Diamond's TYSGM-9 culture medium. After their exposure to x-ray film (16 h) the spots were cut and counted in a scintillation counter. Counting results are given after subtraction of background (18 cpm).
Figure 6:
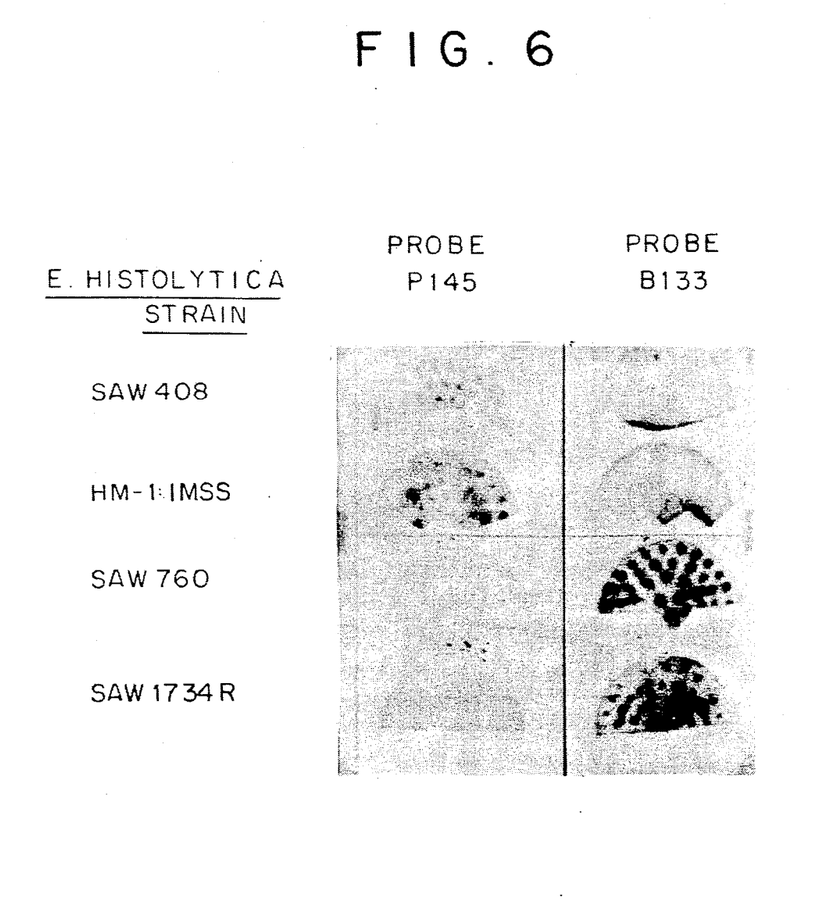
FIG. 6 shows the results of hybridization of *E. histolytica* trophozoites directly on Zetapore membrane filters. Suspensions of trophozoites ($2 \times 10^5$) were filtered with a Buchner funnel and DNA denatured as described in Methods. Filters were cut in halves and hybridized with probes P145 or B133 as described for Southern blots. Strain SAW 408 and HM-1:IMSS had pathogenic zymodemes, whereas SAW 1734R clAR and SAW 760 had non-pathogenic zymodemes.

Restriction enzyme analysis of clone H16 revealed a PvuI fragment of 145 b.p. which was repeated about 15 times. When this fragment, released by digestion with Sau3AI, was subcloned into the BamHI site of pUC-18 and used as a hybridization probe, the pattern shown in FIG. 3b was obtained. Clone P145 hybridized to a subset of the bands visualized by clone H4.4 (FIG. 3a). Interestingly, clone H4.4 has no PvuI sites and hybridizes very weakly with clone P145 (not shown). In addition, hybridization with P145 was observed with dot blots of DNA of xenically grown strain SAW 755 which has pathogenic zymodeme group XIV, but not with that from the non-pathogenic strains SAW 760 or CDC:0784:4 (FIGS. 5, 6).

This exciting finding of sequences specific to isolates of E. histolytica with pathogenic zymodemes prompted the searching and testing of DNA probes derived from isolates with non-pathogenic zymodemes for their specificity.

Figure 4:
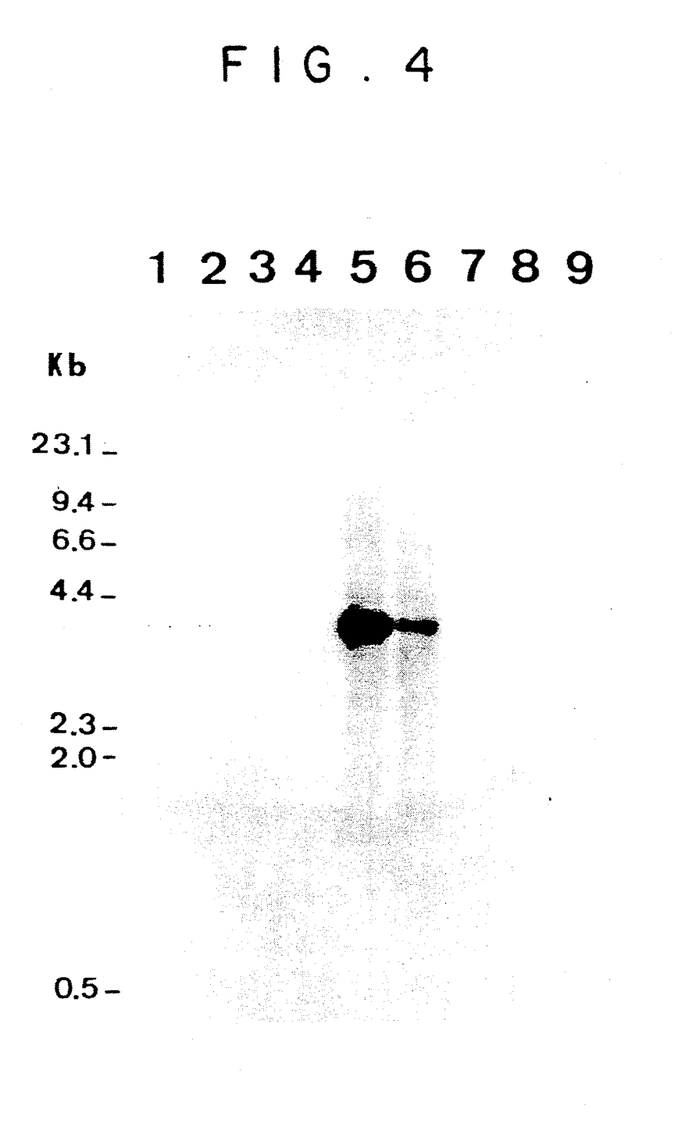
FIG. 4 is a Southern blot hybridization using probe B3.0. This probe hybridizes exclusively to DNA from nonpathogenic isolates of *E. histolytica*. Samples are the same as in FIG. 1.

Probe B3.0 derived from a genomic library of strain SAW 1734R clAR, which has a non-pathogenic zymodeme, hybridized only to DNA of the xenically grown non-pathogenic strains SAW 1734R clAR and WI:1285:1, and not to DNA or any of the pathogenic strains tested (FIG. 4).

Restriction enzyme analysis of clone B3.0 revealed a BamHI fragment of 133 b.p. which was repeated about 15 times. When this fragment (B133) was released, subcloned into the BamHI site of pUC-8 and used as a probe, it hybridized only to DNA of strains SAW 1734R clAR, WI:1285:1, SAW 760 and CDC:0784:4, which had non-pathogenic zymodemes (FIGS. 5, 6). Probe B133 did not hybridize to any of the strains that possessed pathogenic zymodemes, including the xenically grown SAW 755. Patterns of hybridization could be observed either on nuclear DNA dot blots (FIG. 5), Southern blots of EcoRI digested DNA (not shown), or with DNA from intact E. histolytica trophozoites which were filtered through a Zetapore membrane filter (FIG. 6). Counter testing of the same filters with probe P145 revealed that this probe hybridized only with the strains that had pathogenic zymodemes (HM-1:IMSS, SAW 755 and SAW 408) and not with the non-pathogenic ones.

The sensitivity of these hybridization tests indicates that the abundant sequences can be detected in less than 1000 trophozoites after an 18 hour exposure.

Very faint signals were observed in dot blots of DNA from xenically grown strain CDC:0784:4 upon hybridization with probe P145 (FIG. 5) and with strain SAW 755 probed with B133. The total amount of radioactivity found upon counting of the dot blots was less than 1% of that obtained with the other probes (H6.6, P145 or B133) using approximately the same amounts of DNA.

Figure 7:
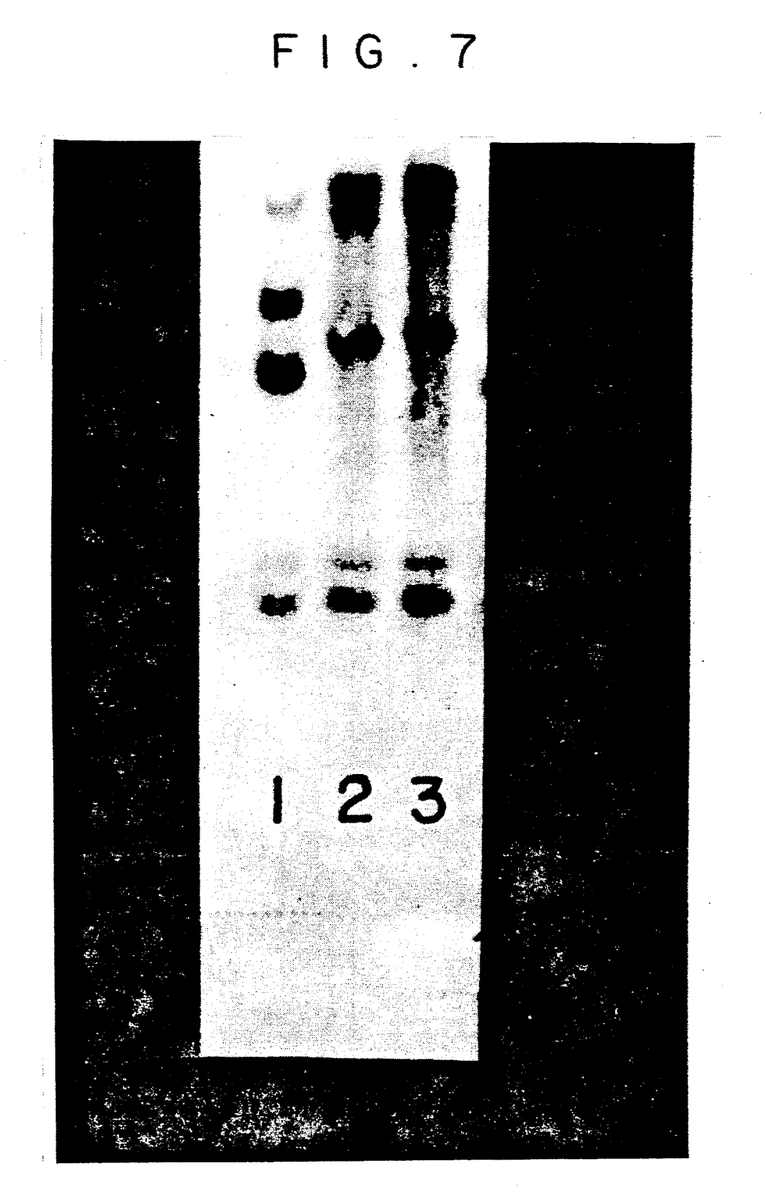
FIG. 7 shows the results of Southern blot hybridization with probe H6.6. EcoRI digested DNA from (1) xenic cultures of DNA from *E. histolytica* strain SAW 1734R clAR originally obtained from P. G. Sargeaunt; (2) axenic cultures of *E. histolytica* SAW 1734R clAR obtained from L. S. Diamond after they had converted to pathogenic zymodeme; and (3) Axenic culture of *E. histolytica* HM-1:IMSS c16.

Previous investigations had shown that during the process of axenization of two isolates possessing non-pathogenic zymodemes (CDC:0784:4 and SAW 1734R clAR), a conversion to pathogenic zymodeme occurred (3,4). Analysis of the hybridization patterns of the DNA from trophozoites of the cloned strain SAW 1734R grown either under axenic conditions (where it has pathogenic zymodeme) or from xenic cultures (where it has non-pathogenic zymodeme) with probe H6.6 on Southern blots (FIG. 7) revealed that the DNA pattern from axenic cultures resembled that of pathogenic strain HM-1:IMSS, whereas the xenic one was similar to that of non-pathogenic WI:1285:1 (FIG. 1). Moreover, the DNA from the axenically grown strain CDC:0784:4 (which had a pathogenic zymodeme) also displayed the hybridization pattern similar to that of a strain with pathogenic zymodemes (FIG. 1), whereas the DNA from xenically cultured trophozoites of the same strain, which had a non-pathogenic zymodeme, hybridized with probe B133 and not with P145 (FIG. 5).

The DNA sequences of both reiterated fragments P145 and B133 were determined after subcloning into phage M13 mp 18 (10). Analysis of the sequences, shown in FIG. 8, shows only about 40% alignment between the two fragments.

The novel DNA probes allow differentiation and classification of E. histolytica isolates according to their pathogenic or non-pathogenic zymodemes. The probes also distinguish between two distinct sets of isolates having the same pathogenic zymodemes, as determined by restriction fragment length polymorphisms. The present probes are the only ones described which provide a test and counter-test for E. histolytica with pathogenic or nonpathogenic zymodemes. They have to be used at high stringency conditions. Those of ordinary skill in the art will understand that "high stringency conditions," as used in the present specification and claims, means that conditions are used of sufficiently high stringency to permit differentiation between the pathogenic and non-pathogenic sequences which, as indicated above, have about 40% homology. Conditions of sufficiently high stringency can easily be empirically determined by those of ordinary skill in the art. As an example, hybridization at stringency conditions at least equivalent to $0.1 \times SSC$, 0.1% SDS for 20 minutes at 65° C. will be operable. On the other hand, hybridization at $0.5 \times SSC$, 0.1% SDC for 20 minutes at 42° C. will be insufficiently stringent.

Two sets of synthetic oligonucleotide probes (20 b.p.) (FIG. 9) having complementary sequences chosen from segments of P145 (FIG. 8) as well as two sets of synthetic oligonucleotide probes (20 b.p.) having complimentary sequences of B133 probe (FIG. 8) were found to exclusively hybridize to DNA of pathogenic or non-pathogenic strains of E. histolytica, respectively, as seen for intact probes P145 and B133 (FIGS. 3–7).

Over 70 different E. histolytica isolates from all over the world have been successfully differentiated by the DNA probes with 100% coincidence with the zymodemes of the amoeba. Non-E. histolytica species do not hybridize.

The sensitivity and selectivity of the assay of the present invention was demonstrated with over 70 isolates of E. histolytica obtained from various parts of the world and the specificity of the test was established by tests with strains which do not belong to the genus E. histolytica. The results were further confirmed by the finding that all symptomatic cases were those of E. histolytica having fast migrating hexokinase isoenzymes, whereas all cases of non-symptomatic nature were those of E. histolytica having slow migrating bands of hexokinase isoenzymes.

While probes of a length of 20 base pairs have been described as being preferred, it should be understood that even shorter probes can be used as long as they can remain hybridized to the target sequence under the hybridization stringency being used. At the present time, 20 base pairs is the practical lower limit, although sequences as small as 17 base pairs can also be used and even smaller probes may be possible.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

Literature cited

1. Walsh, J. A. (1986) "Problems in recognition and diagnosis of amoebiasis. Estimates of the global magnitude of morbidity and mortality", Rev. Infect. Dis, 8:228–238.
2. Sargeaunt, P. G. (1987) "The reliability of E. histolytica zymodemes in clinical diagnosis", Parasitol. Today, 3:40–43.
3. Mirelman, D., R. Bracha, A. Chayen, A. Aust-Kettis, and L. S. Diamond (1986) "E. histolytica: Effect of growth conditions and bacterial associates on isoenzyme patterns and virulence", Exp. Parasitol., 62:142–148.
4. Mirelman, D., R. Bracha, A. Wexler, and A. Chayen (1986) "Changes in isoenzyme patterns of a cloned culture of non-pathogenic E. histolytica during axenization", Infect. Immun., 54:827–832.

5. Diamond, L. S., D. R. Harlow, and C. C. Cunnick (1978) "A new medium for the axenic cultivation of *E. histolytica* and other Entamoeba", *Trans. R. Soc. Trop. Med. Hyg.*, 72:431-432.
6. Diamond, L. S. (1982) "A new liquid medium for xenic cultivation of *E. histolytica* and other lumen dwelling protozo", *J. Protozol.*, 68, 958-959.
7. Huber, M., L. Garfinkel, C. Gitler, D. Mirelman, M. Revel, and S. Rozenblatt (1987) "*E. histolytica*: Cloning and characterization of actin cDNA", *Mol. Biochem. Parasitol.*, 24:227-235.
8. Hanahan, D. (1983) "Studies on transformation of *Escherichia coli* with plasmids", *J. Mol. Biol.*, 166:557-580.
9. Sanger, F., S. Nicklen, and A. R. Coulson (1977) "DNA sequencing with chain termination inhibitors", *Proc. Natl. Acad Sci USA.*, 74:5463-5467.
10. Messing, J. (1983) "New M13 vectors for cloning", *Methods Enzymol.*, 101:20-78.
11. Lipman, D. J. and W. R. Pearson (1985) "Rapid and sensitive protein similarity searches", *Science*, 227:1435-1441.
12. Bhattacharya, S., A. Bhattacharya, and L. S. Diamond (1988) "Comparison of repeated DNA from strains of *E. histolytica* and other *Entamoeba*", *Mol. Biochem. Parasitol.*, 27:257-262. Entner, N. (1971) "'Mating' in *E. histolytica*?", *Nature (New Biol.)*, 232:256.

We claim:

1. A DNA probe for detecting the presence of isolates of pathogenic *E. histolytica*, consisting essentially of a DNA sequence which is complementary or identical to the sequence shown in FIG. 9A or a portion thereof which, under high stringency conditions, selectively hybridizes to the DNA of pathogenic *E. histolytica* and not to the DNA of non-pathogenic *E. histolytica*.

2. A DNA probe in accordance with claim 1, wherein said DNA sequence is a portion of the sequence shown in FIG. 8A which is relatively rich in guanosine and cytosine residues.

3. A DNA probe in accordance with claim 1, wherein said sequence has about 20 bases.

4. A DNA probe in accordance with claim 1, wherein said sequence contains a portion which is complementary or identical to bases 1 to 20 or 119 to 138 of the sequence shown in FIG. 8A.

5. A DNA probe in accordance with claim 1 wherein said probe consists essentially of a sequence which is complementary or identical to bases 1 to 20 or 119 to 138 of the sequence shown in FIG. 8A.

6. A DNA probe for detecting the presence of isolates of non-pathogenic *E. histolytica*, consisting essentially of a DNA sequence which is complementary or identical to the sequence shown in FIG. 8B or a portion thereof which, under high stringency conditions, selectively hybridizes to the DNA of non-pathogenic *E. histolytica* and not to the DNA of pathogenic *E. histolytica*.

7. A DNA probe in accordance with claim 6, wherein said DNA sequence is a portion of the sequence shown in FIG. 8B which is relatively rich in guanosine and cytosine residues.

8. A DNA probe in accordance with claim 6, wherein said sequence has about 20 bases.

9. A DNA probe in accordance with claim 6, wherein said sequence contains a portion which is complementary or identical to bases 44 to 63 or 110 to 129 of the sequence shown in FIG. 8B.

10. A DNA probe in accordance with claim 6 wherein said probe consists essentially of a sequence which is complementary or identical to bases 44 to 63 or 110 to 129 of the sequence shown in FIG. 8B.

11. An assay method for the detection and identification of pathogenic strains of *E. histolytica*, comprising:
   extracting nucleic acid from an *E. histolytica* amoeba to be examined;
   immobilizing said nucleic acid on a suitable support; and
   determining whether a probe in accordance with claim 1 hybridizes with said nucleic acid under high stringency hybridization conditions,
   whereby a finding of hybridization establishes that the amoeba being examined is a pathogenic strain.

12. An assay in accordance with claim 11, wherein said probe is labeled in a suitable manner with a radioactive tag, enzymatic substrate liquid, or other biological recognition tag.

13. An assay method for the detection and identification of non-pathogenic strains of *E. histolytica*, comprising:
   extracting nucleic acid from an *E. histolytica* amoeba to be examined;
   immobilizing said nucleic acid on a suitable support; and
   determining whether a probe in accordance with claim 6 hybridizes with said nucleic acid under high stringency hybridization conditions,
   whereby a finding of hybridization establishes that the amoeba being examined is a non-pathogenic strain.

14. An assay in accordance with claim 13, wherein said probe is labeled in a suitable manner with a radioactive tag, enzymatic substrate ligand, or other biological recognition tag.

15. A kit for carrying out an assay for the detection and identification of pathogenic strains of *E. histolytica*, comprising a supply of a probe in accordance with claim 1, suitable buffers and solvents, and a suitable support for said probe, buffer and solvents.

16. A kit in accordance with claim 15, wherein said probe is labeled with a radioactive tag, enzymatic substrate ligand, or other biological recognition tag, and further including detection means for said labeled probe.

17. A kit for carrying out an assay for the detection and identification of non-pathogenic strains of *E. histolytica*, comprising a supply of a probe in accordance with claim 6, suitable buffers and solvents, and a suitable support for said probe, buffer and solvents.

18. A kit in accordance with claim 17, wherein said probe is labeled with a radioactive tag, enzymatic substrate ligand, or other biological recognition tag, and further including detection means for said labeled probe.

* * * * *

UNITED STATES PATENT AND TRADEMARK OFFICE
CERTIFICATE OF CORRECTION

PATENT NO. : 5,071,742    Page 1 of 2
DATED     : December 10, 1991
INVENTOR(S) : MIRELMAN et al.

It is certified that error appears in the above-identified patent and that said Letters Patent is hereby corrected as shown below:

ON THE TITLE PAGE:

[75] Inventors:  line, 6    Delete "Michel Renel", insert therefor -- Michel Revel --

On Face of Patent:

Under OTHER PUBLICATIONS,

Line 1    Delete "Panasitology,", insert therefor, -- Parasitology, --

Lines 6 and 7    Delete "Geomic DNA Differneces between Pathogenic an Nonpathogenic Entamoeba Histoyltica;", insert therefor -- Genomic DNA Differences between Pathogenic and Nonpathogenic Entamoeba Histolytica; --

Line 11    Delete "Entameoba", insert therefor -- Entamoeba --

Lines 16 and 17    Delete "(copy not attached)."

UNITED STATES PATENT AND TRADEMARK OFFICE
CERTIFICATE OF CORRECTION

PATENT NO. : 5,071,742

DATED : December 10, 1991

INVENTOR(S) : MIRELMAN et al.

Figure 8A:
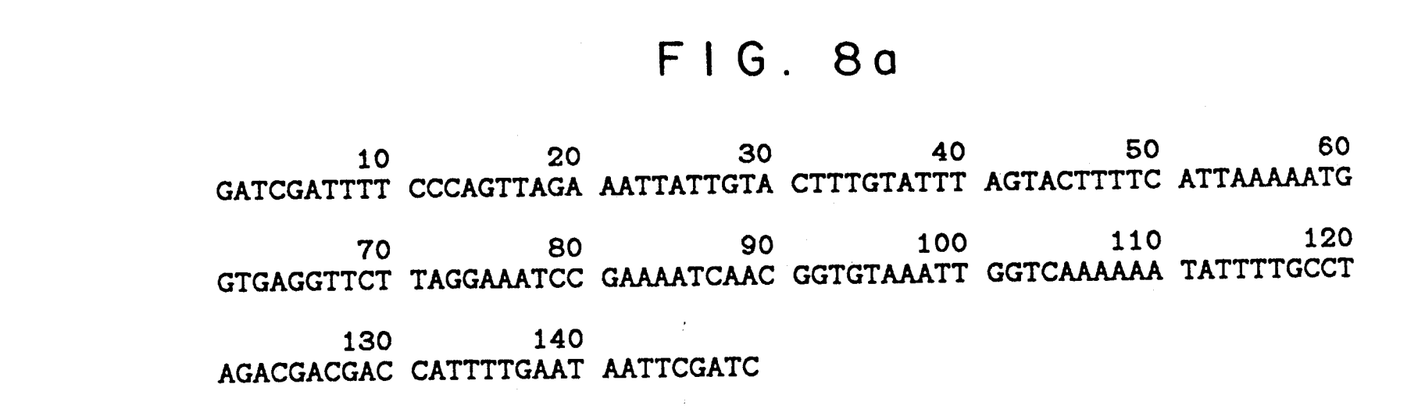
FIG. 8 shows the DNA sequences of (a) probe P145 isolated from *E. histolytica* HM-1:IMSS c16 and (b) probe B133 obtained from *E. histolytica* strain SAW 1734R clAR, possessing non-pathogenic zymodeme. Sequences were determined by the dideoxy chain termination method of Sanger (9) as described in Materials and Methods.
Figure 8B:
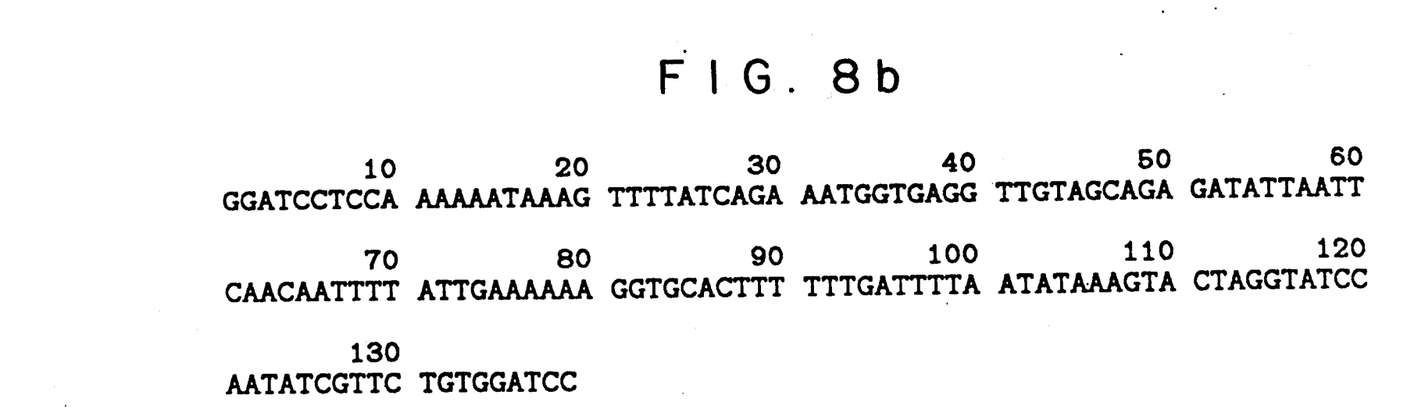
Figure 9:
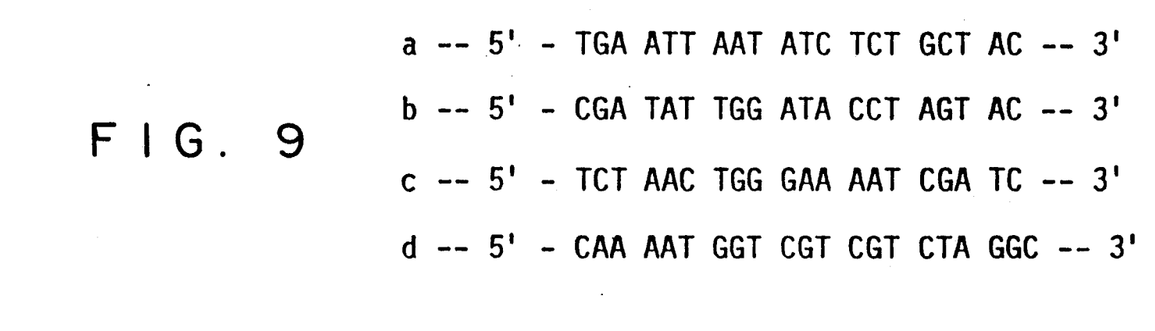
FIG. 9 shows the sequences of the following synthetic oligonucleotide probes:
a) Complementary sequence to segment containing nucleotide sequence 43-62 of B133 element (see FIG. 8).
b) Complementary sequence to segment containing nucleotide sequence 108-127 of B133 element (see FIG. 8).
c) Complementary Sequence to segment containing nucleotide sequence 1-20 of P145 element (see FIG. 8).
d) Complementary sequence to segment containing nucleotide sequence 117-137 of P145 element (see FIG. 8).

It is certified that error appears in the above-identified patent and that said Letters Patent is hereby corrected as shown below:

Claim 1, Column 9, line 34    Delete "FIG. 9A", insert therefor -- FIG. 8A --

Claim 12, Column 10, line 24    Delete "liquid", insert therefor -- ligand --

Signed and Sealed this

Twenty-first Day of September, 1993

Attest:

BRUCE LEHMAN

Attesting Officer    Commissioner of Patents and Trademarks